(12) United States Patent
Zhang

(10) Patent No.: US 8,069,702 B2
(45) Date of Patent: Dec. 6, 2011

(54) ROLLING BALL TACK MEASURING APPARATUS

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 240 days.

(21) Appl. No.: 12/622,340

(22) Filed: Nov. 19, 2009

(65) Prior Publication Data

US 2011/0011173 A1 Jan. 20, 2011

(30) Foreign Application Priority Data

Jul. 15, 2009 (CN) .......................... 2009 1 0304351

(51) Int. Cl.
*G01N 3/56* (2006.01)
*G01N 19/02* (2006.01)
*G01N 19/04* (2006.01)

(52) U.S. Cl. .......................................... 73/9; 73/150 A

(58) Field of Classification Search ............. 73/9, 150 A
See application file for complete search history.

(56) References Cited

U.S. PATENT DOCUMENTS 5,635,623 A * 6/1997 Simon .................................. 73/9

FOREIGN PATENT DOCUMENTS

SU 974164 A * 11/1982

OTHER PUBLICATIONS

Author: R. A. Roberts, Title: Review of Methods for the Measurement of Tack, Publisher: Pira International-National Physical Laboratory, Edition: Project PAJ1: Failure criteria and their application to Visco-Elastic/Visco-Plastic materials, Report 5, Date: Sep. 1997, pp. 1-11.*

* cited by examiner

*Primary Examiner* — Lisa Caputo
*Assistant Examiner* — Roger Hernandez-Prewitt
(74) *Attorney, Agent, or Firm* — Altis Law Group, Inc.

(57) ABSTRACT

A measuring apparatus to measure adhesion of a tape includes a supporting plate slanting related to horizon, and a ball. The tape is attached to the supporting plate with an adhesive surface opposite to the supporting plate. The ball rolls on the tape along the supporting plate. The ball would be held by the tape according to the weight of the ball and the adhesion of the tape, thereby assessing the adhesion. The measuring apparatus further includes a base, a positioning mechanism mounted to the supporting plate, and an angle-adjusting mechanism engaging with the base and the supporting plate and capable of rotating related to the base to adjust a slanting angle of the supporting plate. The positioning mechanism includes a frame to releasably hold and position the ball.

10 Claims, 5 Drawing Sheets

ROLLING BALL TACK MEASURING APPARATUS

BACKGROUND

1. Technical Field

The present disclosure relates to a measuring apparatus to measure adhesion of a tape.

2. Description of the Related Art

In manufacturing, a tape is often used to adhere to a surface of a product to protect the surface from being scratched. If adhesion of the tape is too weak, the tape cannot be attached firmly to the product and tends be accidently detached from the product. If the adhesion of the tape is too strong, coating on the surface of the product may be damaged in detaching of the tape from the product. Therefore, measuring the adhesion of the tape is necessary for choosing a tape with proper adhesion.

In a conventional measuring method, a tape is fixedly spread on a plate slantingly placed related to horizon, with an adhesive surface of the tape opposite to the plate. Balls with different weights roll along the plate from a beginning point, the adhesion of the tape is assessed according to the weightiest ball able to be held by the adhesive surface of the tap, for example, the ball is stopped by the tape or the ball rolls down along the tape slowly enough.

One disadvantage of the conventional measuring method described above is that an slanting angle of the plate has to be calibrated with gauge. Another disadvantage of the conventional method is that operators need to hold the balls at the beginning point before the test starts. Therefore, the conventional measuring method is inefficient and laborious.

DETAILED DESCRIPTION

Figure 1:
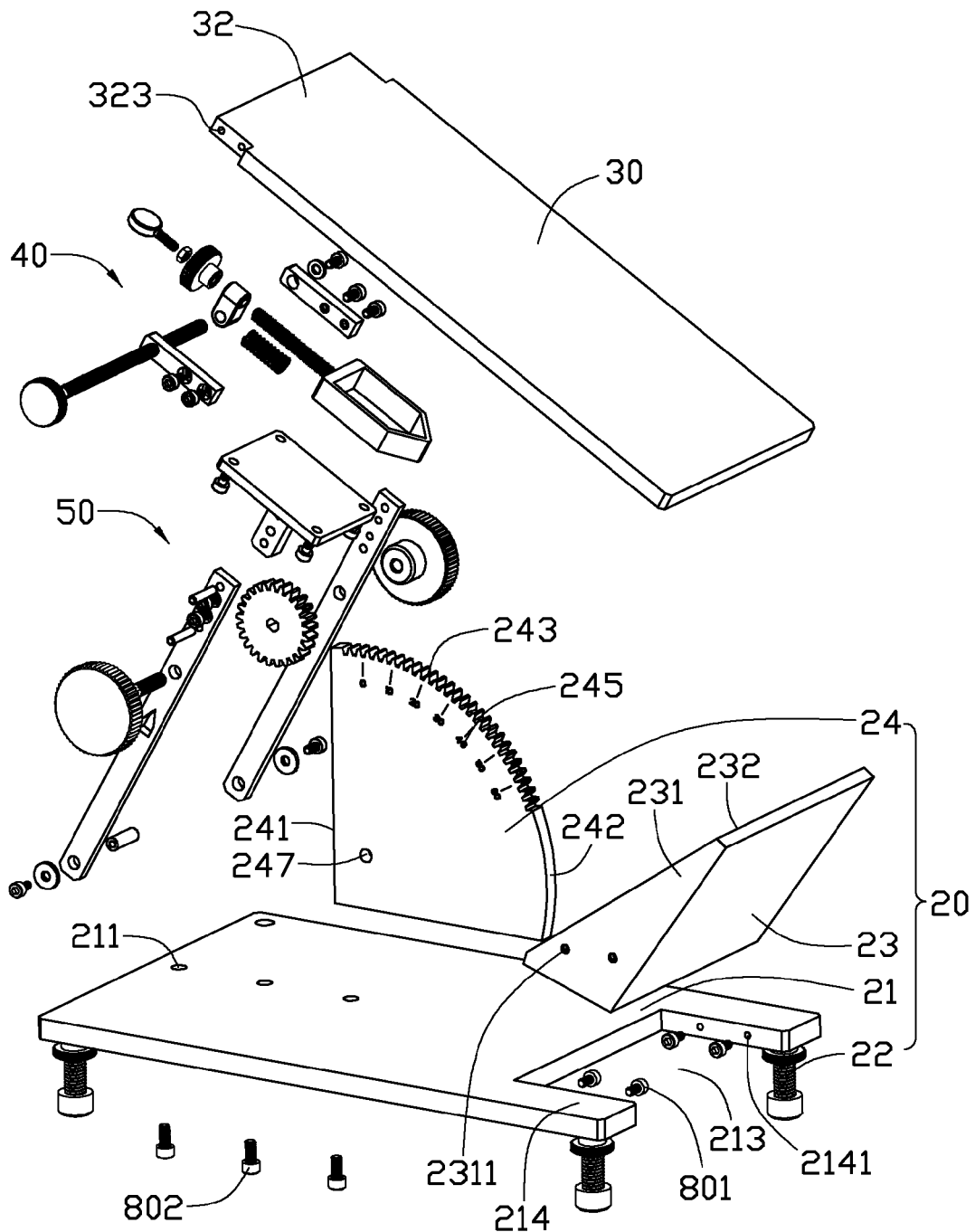
FIG. 1 is an exploded, isometric view of an exemplary embodiment of a measuring apparatus, the measuring apparatus includes a positioning mechanism and an angle-adjusting mechanism.
Figure 5:
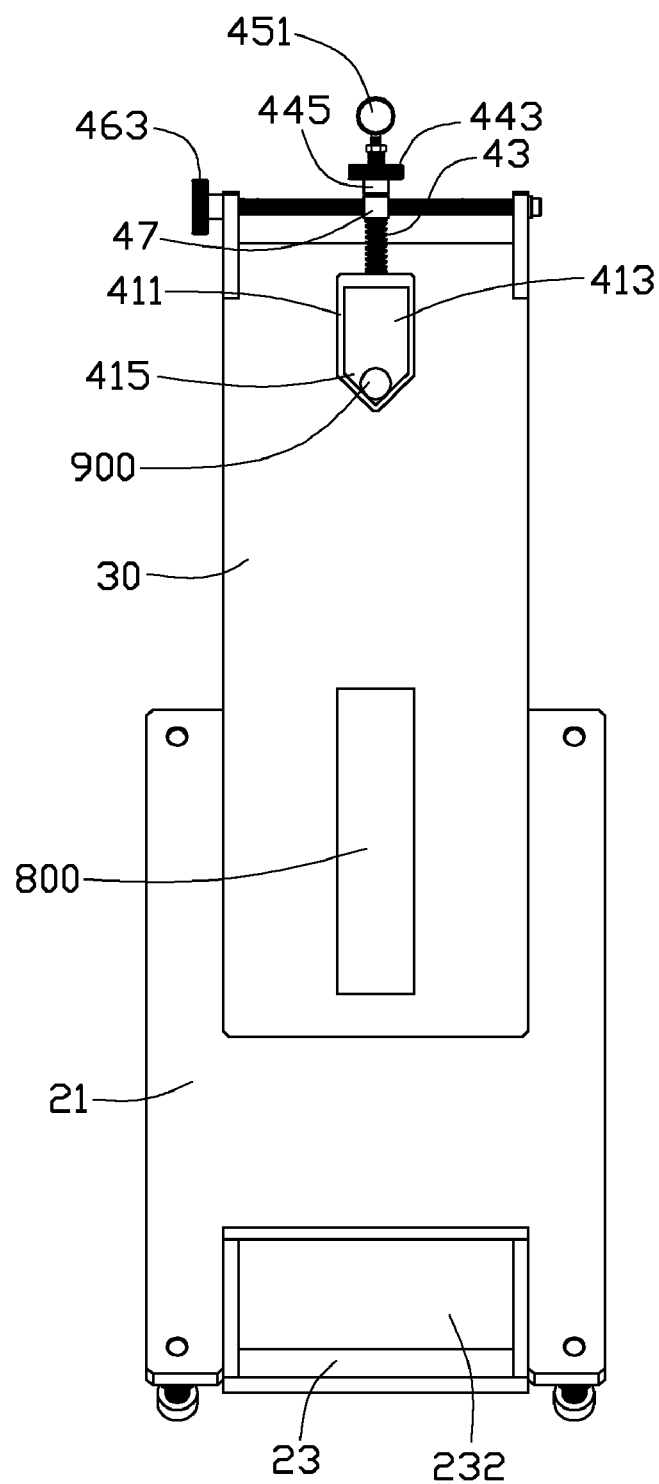
FIG. 5 is a top planar view of the measuring apparatus of FIG. 4, but showing the measuring apparatus in a use state.

Referring to FIG. 1, in an exemplary embodiment, an measuring apparatus is provided to measure adhesion of a tape 800 (shown in FIG. 5). The measuring apparatus includes a base 20, a supporting plate 30, a positioning mechanism 40, and an angle-adjusting mechanism 50.

The base 20 includes a platform 21, four supporting members 22 perpendicularly extending down from four corners of the platform 21, a gathering box 23, and a sustaining plate 24. A plurality of fixing holes 211 is defined in the platform 21, adjacent to a first end of the platform 21. A rectangular-shaped mounting notch 213 is defined in a second end opposite to the first end of the platform 21. Each of opposite sides bounding the mounting notch 213 defines two screw holes 2141. The gathering box 23 is substantially wedge-shaped, and includes two opposite rectangular-shaped sidewalls 231, and an accessing opening 232 defined in a side of the gathering box 23 between the two sidewalls 231. Each of the two sidewalls 231 defines two alignment holes 2311. The sustaining plate 24 is substantially shaped like a quarter of a circle, and includes two right-angled straight sides 241, and a curved side 242 with opposite ends connected to the two straight sides 241, respectively. One of the straight sides 241 defines a plurality of screw holes (not shown in the drawings). An engagement interface 243 including a plurality of teeth is formed on the curved side 242. A plurality of angle marks 245 is formed on one of opposite side surfaces of the sustaining plate 24, and distributed along the curved side 242. A mounting hole 247 is defined in the sustaining plate 24, adjacent to a joint of the two straight sides 241.

The supporting plate 30 is substantially rectangular-shaped, and includes a mounting portion 32 at an end of the supporting plate 30, narrower than the supporting plate 30. Each of opposite sidewalls of the mounting portions 32 defines two screw holes 323. A plurality of screw holes (not shown in the drawings) is defined in a bottom surface of the supporting plate 30.

Figure 2:
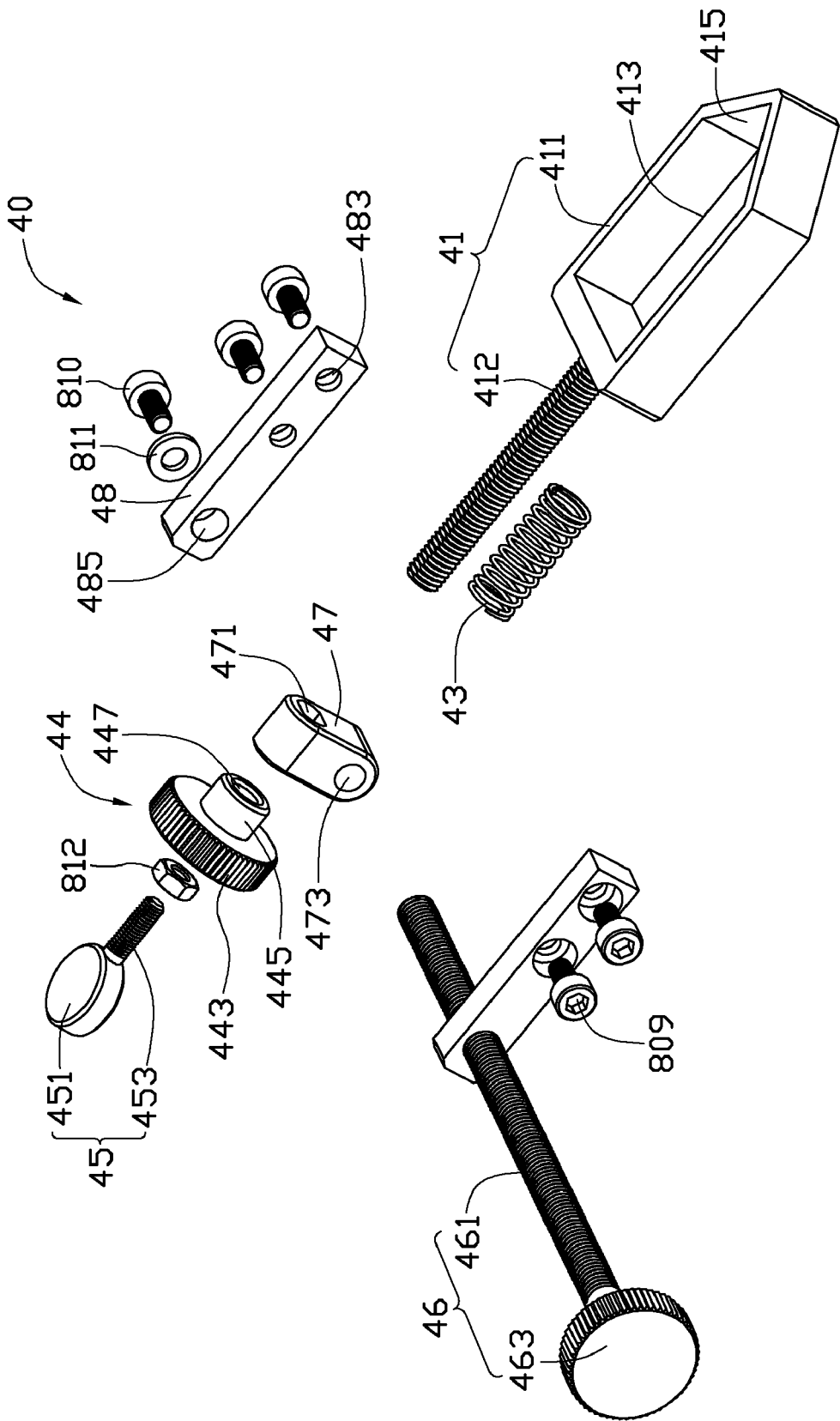
FIG. 2 is an enlarged, exploded view of the positioning mechanism of FIG. 1.

Referring to FIG. 2, the positioning mechanism 40 includes a holding member 41, an elastic member such as a spring 43, a rotating button 44, a first operating member 45, a second operating member 46, a guiding member 47, and two securing members 48. The holding member 41 includes a frame 411 and a first threaded post 412 extending from the frame 411. The frame 411 includes five sidewalls, which cooperatively bound a receiving space (not labeled). The receiving space includes a rectangular-shaped accessing portion 413 adjacent to the first threaded post 412, and a triangular-shaped positioning portion 415 communicating with the accessing portion 413 and opposite to the first threaded post 412. A cross section of the first threaded post 412 is double-D shaped, and an axial screw hole (not shown in the drawings) is defined in a distal end of the first threaded post 412. The rotating button 44 includes a disc-shaped manipulating portion 443, and an abutment portion 445 protruding from a middle of a side of the manipulating portion 443. A threaded through hole 447 is axially defined in the rotating button 44, through the manipulating portion 443 and the abutment portion 445. The first operating member 45 includes a disc-shaped knob 451 and a threaded coupling portion 453 extending from a circumference of the knob 451. The second operating member 46 includes a disc-shaped rotating portion 463, and a second threaded post 461 perpendicularly extending from a side of the rotating portion 463. A screw hole (not shown in the drawings) is axially defined in a distal end of the second threaded post 461. A first guiding hole 471 and a second guiding hole 473 are defined in the guiding member 47, respectively adjacent to two opposite ends of the guiding member 47, perpendicular to each other. A cross section of the first guiding hole 47 is double-D shaped. The second guiding hole 473 is threaded. Each of the securing members 48 is substantially bar-shaped, with two securing holes 483 defined therein adjacent to a first end of the securing member 48, and a coupling hole 485 defined therein adjacent to a second end opposite to the first end of the securing member 48.

Figure 3:
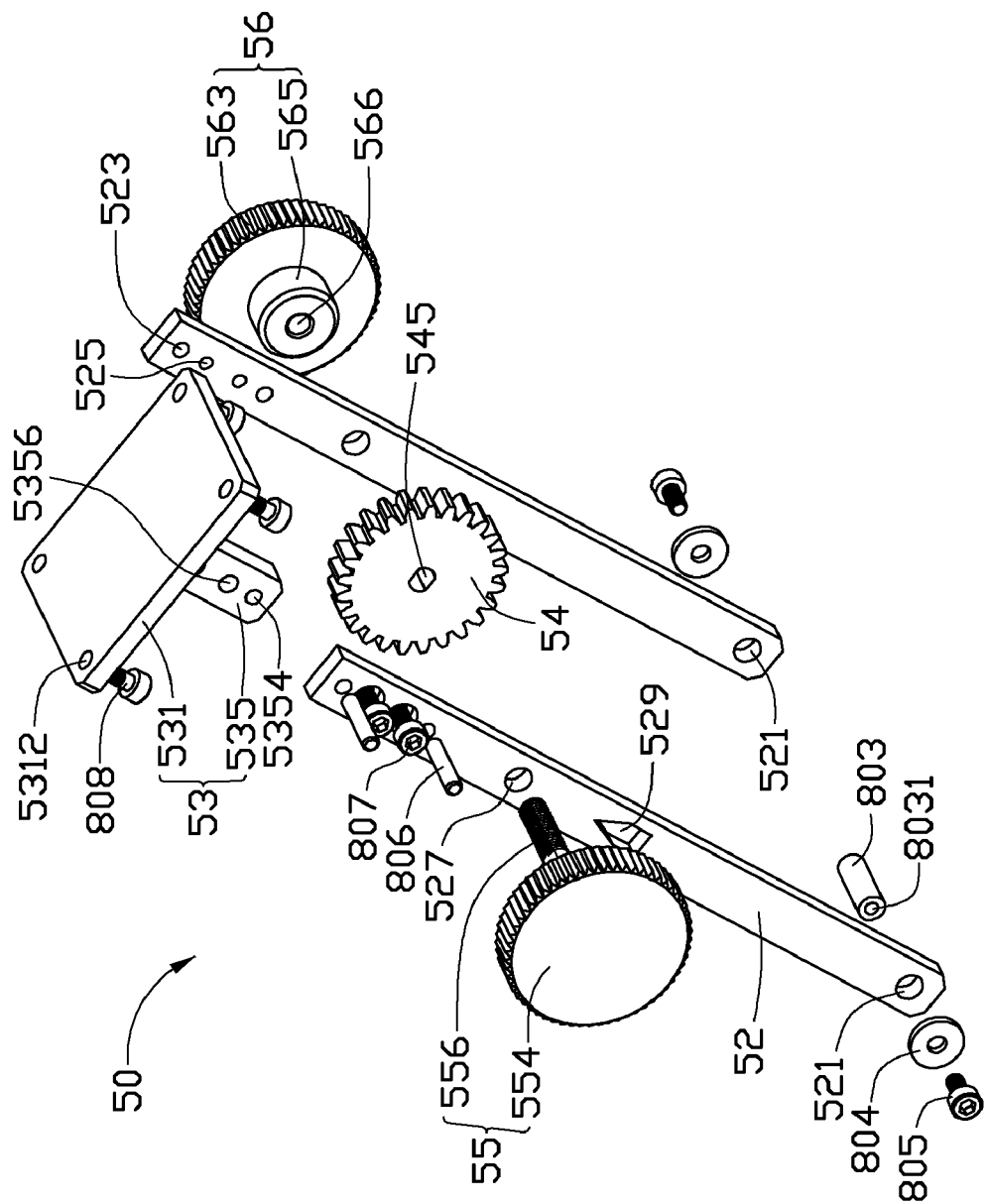
FIG. 3 is an enlarged, exploded view of the angle-adjusting mechanism of FIG. 1.

Referring to FIG. 3, the angle-adjusting mechanism 50 includes two arms 52, a connecting bracket 53, a gear 54, a handle 55, and a fastening member 56. Each of the arms 52 defines a pivot hole 521 adjacent to a first end of the arm 52, and two fixing holes 523 and two screw holes 525 adjacent to a second end opposite to the first end of the arm 52, and a rotating hole 527 in a middle of the arm 52. The two screw holes 525 are arranged between the two fixing holes 523. One of the arms 52 further defines an opening 529 adjacent to the rotating hole 527. The connecting bracket 53 includes a connecting board 531 and a connecting bar 535 perpendicular extending from the connecting board 531. The connecting board 531 defines a plurality of alignment holes 5312. The connecting bar 535 defines two fixing holes 5354 respectively adjacent to opposite ends of the connecting bar 535, and two connecting holes 5356 arranged between the two fixing holes 5354. The gear 54 defines an double-D shaped retaining hole 545. The handle 55 includes a disc-shaped manipulating portion 554, and a threaded post 556 with a double-D shaped cross section perpendicularly extending from the manipulating portion 554. The fastening member 56 includes a disc-shaped handling portion 563 and a cylindrical-shaped engagement portion 565 perpendicularly protruding from the handling portion 563. A screw hole 566 is axially defined in the engagement portion 565.

Figure 4:
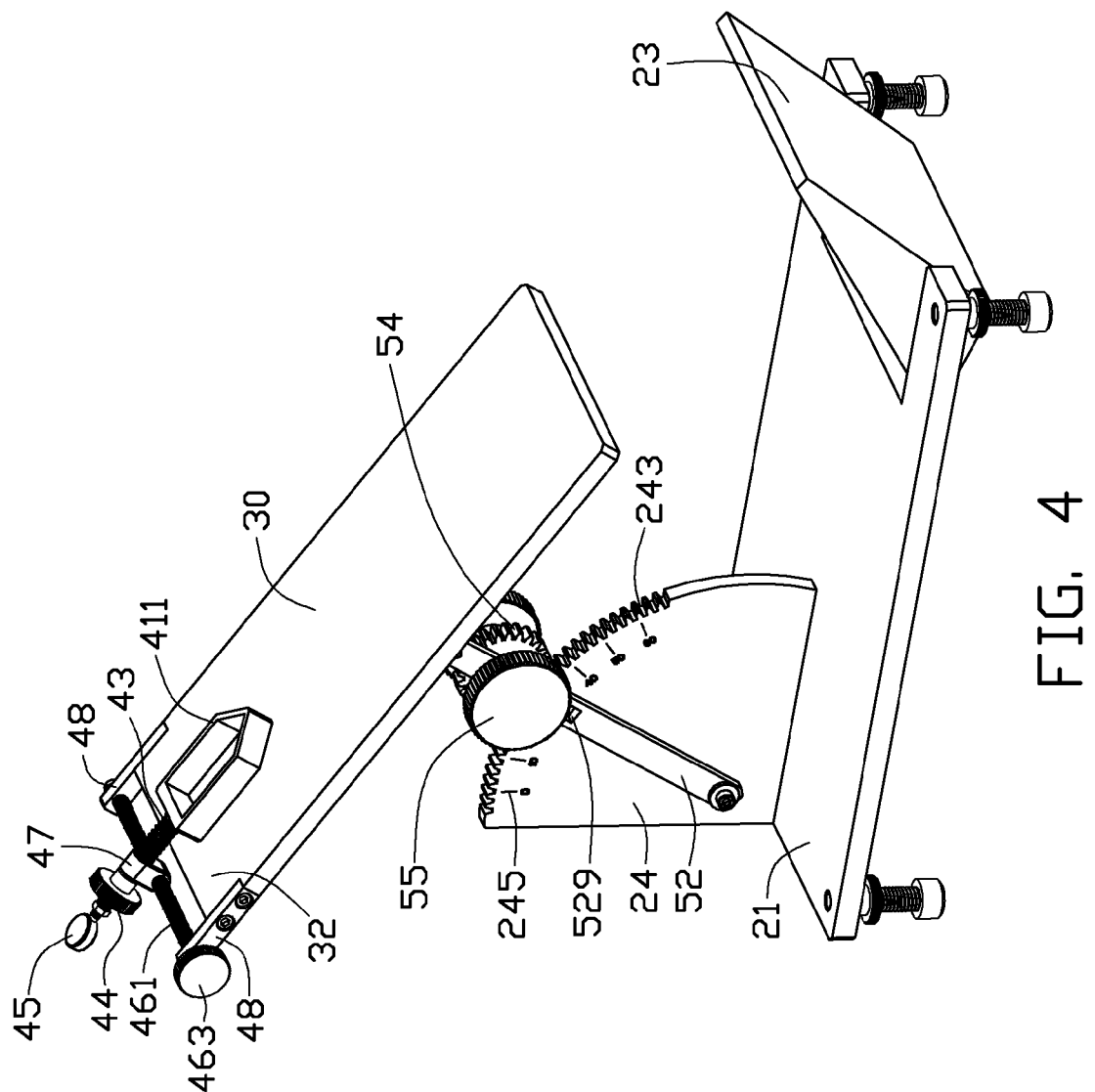
FIG. 4 is an assembled, isometric view of the measuring apparatus of FIG. 1.

Referring to FIG. 4, in assembly of the base 20, the gathering box 23 is engaged in the mounting notch 213 of the platform 21, with the alignment holes 2311 of the gathering box 23 aligned with the screw holes 2141 of the platform 21. Four screws 801 pass through the alignment holes 2311 of the gathering box 23 and engage in the corresponding screw holes 2141 of the platform 21, from the opening 232, to retain the gathering box 23 to the platform 21. The sustaining plate 24 is perpendicularly mounted to the platform 21, with a plurality of screws 802 passing through the fixing holes 211 of the platform 21 and engaged in the corresponding screw holes in one of the straight sides 241 of the sustaining plate 24.

To assemble the angle-adjusting mechanism 50 to the base 20, the threaded post 556 of the handle 55 sequentially passes through the rotating hole 527 of one of the arms 52, the retaining hole 545 of the gear 54, and the rotating hole 527 of the other arm 52, to engage in the screw hole 566 of the fastening member 56. The arms 52 are manipulated to sandwich the sustaining plate 24 therebetween and make the gear 54 to mesh with the engagement interface 243 of the sustaining plate 24. A pin 803 defining an axial screw hole 8031 fixedly passes through the mounting hole 247 of the sustaining plate 24, with opposite ends of the pin 803 movably engaged in the pivot holes 521 of the respective arms 52. Two screws 805, each fitting about a washer 804, respectively engage in the screw hole 8031 of the pin 803 from opposite ends of the pin 803, therefore, the two arms 52 are pivotably mounted to the sustaining plate 24 about the pin 803. With rotation of the arms 52, one of the angle marks 245 can be exposed through the opening 529 of one of the arms 52. The connecting bar 535 of the connecting bracket 53 is inserted between the two arms 52, from the second ends of the arms 52. Two pins 806 are respectively fixedly engaged in the fixing holes 523 of the arms and the corresponding fixing holes 5354 of the connecting bar 535 of the connecting bracket 53. Two screws 807 pass through the two connecting holes 5356 and engage in the corresponding screw holes 525 of the two arms 52. Therefore, the connecting bracket 53 is retained to the second ends of the arms 52.

A plurality of screws 808 passes through the plurality of alignment holes 5312 of the connecting board 531 of the connecting bracket 53 and engages in the corresponding screw holes of the supporting plate 30 to connect the supporting plate 30 to the connecting bracket 53.

To mount the positioning mechanism 40 to the supporting plate 30, the two securing members 48 are respectively retained to opposite sides of the mounting portions 32 of the supporting plate 30, with four screws 809 correspondingly passing through the securing holes 483 of the two securing members 48 and engaging in the screw holes 323 of the supporting plate 30. The second threaded post 461 of the second operating member 46 sequentially passes through the coupling hole 485 of one of the securing members 48 at a left side of the supporting plate 30, the second guiding hole 473 of the guiding member 47, and the coupling hole 485 of the other securing member 48 at a right side of the supporting plate 30. A screw 810 passes through a washer 811 and engages in the screw hole defined in the distal end of the second threaded post 461, thereby preventing the second operating member 46 from being accidently released from the securing members 48 and the guiding member 47. The first threaded post 412 of the holding member 41 passes through the spring 43 and the first guiding hole 471 of the guiding member 47, and engages in the through hole 447 of the rotating button 44. The coupling portion 453 of the first operating member 45 passes through a nut 812 and engages in the screw hole defined in the distal end of the first threaded post 412. The nut 812 is tightened to retain the first operating member 45 to the distal end of the first threaded post 412. Opposite ends of the spring 43 resist against the frame 411 and the guiding member 47, to bias the guiding member 47 to abut against the abutment portion 445 of the rotating button 44. The frame 411 of the holding member 41 is seated on the supporting plate 30.

Referring to FIG. 5, in use, the tape 800 is fixedly spread on the supporting plate 30, with an adhesive surface opposite to the supporting plate 30. A ball 900 is put into the frame 411 through the accessing portion 413, and rolls into the positioning portion 415 of the frame 411. The rotating portion 463 of the second operating member 46 is rotated, the second threaded post 461 engagingly rotates in the second guiding hole 473 of the guiding member 47 to make the guiding member 47 to slide along the second threaded post 461. Therefore, the holding member 41, together with the ball 900, moves with the guiding member 47 in a transverse direction of the supporting plate 30, to make the ball 900 align with the tape 800. Because of the double-D shaped cross sections of the first guiding hole 471 and the first threaded post 412 of the holding member 41, the first threaded post 412 cannot rotate in the first guiding hole 471. The first threaded post 412 engagingly slides along the through hole 447, by rotating the manipulating portion 443 of the rotating button 44, to make the ball 900 move in a longitudinal direction of the supporting plate 30 to a position with a desired distance from the tape 800. The manipulating portion 554 of the handle 55 is rotated, the gear 54 rotates with the rotating of the handle 55, and engagingly moves along the engagement interface 243 of the sustaining plate 24. Therefore, the arms 52 is pivoted about the pin 803 to enable an adjustment of a slanting angle of the supporting plate 30 related to horizon. Since current slanting angle of the supporting plate 30 is reflected by one of the angle marks 245 exposed through the opening 529 of one of the arms 52, it is easy to precisely adjust the slanting angle of the supporting plate 30. When a desired slanting angle of the supporting plate 30 is acquired, the fastening member 56 is tightened to keep the arms 52 in position. The knob 451 of the operating member 45 is pressed to rotate the guiding member 47, thereby raising the frame 411 of the holding member 41 away from the supporting plate 30. The ball 900 is released from the frame 411 and rolls along the supporting plate 30. If the ball 900 is held by the tape 800, another ball with a greater weight is provided for the measuring process description above. If the ball 900 is not held by the tape 800, another ball with a smaller weight is provided for the measuring process description above. Therefore, the weightiest ball able to be held by the tape 800 can be determined to make an assessment of the adhesion of the tape 800. In the measuring process, the ball 900 falling down from the supporting plate 30 will be received in the gathering box 23 to make it convenient to pick up the ball 900.

It is believed that the present embodiment and its advantages will be understood from the foregoing description, and it will be apparent that various changes may be made thereto without departing from the spirit and scope of the description or sacrificing all of its material advantages, the example hereinbefore described merely being exemplary embodiments.

What is claimed is:

1. A measuring apparatus to measure adhesion of a tape, the measuring apparatus comprising:
    a base;
    a supporting plate slanting related to horizon, the tape fixedly spread on the supporting plate with an adhesive surface of the supporting plate opposite to the supporting plate;
    an angle-adjusting mechanism engaging with the base and the supporting plate, the angle-adjusting mechanism comprising an arm with a first end pivotably connected to the base and a second end fixedly connected to the supporting plate, therefore, the angle-adjusting mechanism enabling adjustment of an slanting angle of the supporting plate related to horizon; and
    a positioning mechanism comprising a holding member movably mounted to the supporting plate, the holding member comprising a frame for holding and releasing a ball.

2. The measuring apparatus of claim 1, wherein the positioning mechanism further comprises two securing members fixed to opposite sides of the supporting plate, and a guiding member rotatably arranged between the two securing members, the holding member further comprises a first threaded post extending from the frame and slidably engaging with the guiding member.

3. The measuring apparatus of claim 2, wherein the positioning mechanism further comprises an elastic member placed around the first threaded post and a rotating button engaging with the first threaded post, opposite ends of the elastic member resist against the frame and the guiding member, respectively, the rotating button abuts against a side opposite to the elastic member of the guiding member.

4. The measuring apparatus of claim 3, wherein the guiding member defines a first guiding hole with a double-D shaped cross section, a cross section of the first threaded post of the holding member is double-D shaped, passing through the first guiding hole of the guiding member.

5. The measuring apparatus of claim 2, wherein the positioning mechanism further comprises a first operating member mounted to a distal end of the first threaded post of the holding member.

6. The measuring apparatus of claim 5, wherein the positioning mechanism further comprises a second operating member, the guiding member defines a threaded second guiding hole, each of the securing members defines a coupling hole, the second operating member comprises a second threaded post engagingly passing through the second guiding member, and rotatably received in the coupling holes of the two securing members.

7. The measuring apparatus of claim 1, wherein the base comprises a platform and a sustaining plate perpendicularly disposed on the platform, the first end of the arm of the angle-adjusting mechanism pivotably connected to the sustaining plate.

8. The measuring apparatus of claim 7, wherein the angle-adjusting mechanism further comprises a gear coupled to the arm, the sustaining member forms an engagement interface meshing with the gear.

9. The measuring apparatus of claim 7, wherein the angle-adjusting mechanism further comprises a handle, the handle comprises a manipulating portion and a threaded post passing through the arm and retained in the gear.

10. The measuring apparatus of claim 7, wherein a plurality of angle marks is formed on the sustaining plate, the arm defines an opening to expose one of the plurality of angle marks.

* * * * *